United States Patent
Dayton

(10) Patent No.: US 10,092,664 B2
(45) Date of Patent: Oct. 9, 2018

(54) DECONTAMINATION COVER FOR DECONTAMINATING AN OBJECT

(71) Applicant: Daylight Medical, Inc., Middleburg Heights, OH (US)

(72) Inventor: Roderick M. Dayton, Strongsville, OH (US)

(73) Assignee: Diversey, Inc., Charlotte, NC (US)

( * ) Notice: Subject to any disclaimer, the term of this patent is extended or adjusted under 35 U.S.C. 154(b) by 0 days.

(21) Appl. No.: 15/209,796

(22) Filed: Jul. 14, 2016

(65) Prior Publication Data

US 2016/0317687 A1    Nov. 3, 2016

Related U.S. Application Data

(63) Continuation of application No. PCT/US2015/056207, filed on Oct. 19, 2015.

(60) Provisional application No. 62/065,198, filed on Oct. 17, 2014.

(51) Int. Cl.
*A61N 5/06* (2006.01)
*A61L 2/10* (2006.01)

(52) U.S. Cl.
CPC .............. *A61L 2/10* (2013.01); *A61L 2202/11* (2013.01); *A61L 2202/16* (2013.01)

(58) Field of Classification Search
None
See application file for complete search history.

(56) References Cited

U.S. PATENT DOCUMENTS

| | | | | |
|---|---|---|---|---|
| 5,173,967 A | * | 12/1992 | Carter | A41D 13/0543 2/16 |
| 8,444,918 B2 | * | 5/2013 | Tanaka | C02F 1/325 210/748.1 |
| 8,710,460 B2 | * | 4/2014 | Dayton | A61L 2/10 250/455.11 |
| 2007/0179574 A1 | * | 8/2007 | Elliott | A61N 5/0616 607/94 |

(Continued)

FOREIGN PATENT DOCUMENTS

| JP | 2007075149 A | * | 3/2007 |
|---|---|---|---|
| KR | 20140065028 | | 5/2014 |

(Continued)

OTHER PUBLICATIONS

International Search Report and Written Opinion dated Jan. 14, 2016 for PCT/US2015/056207.

*Primary Examiner* — Andrew Smyth
(74) *Attorney, Agent, or Firm* — Cooper Legal Group, LLC

(57) ABSTRACT

Provided is a decontamination cover to be applied over an object to be decontaminated. The decontamination cover includes a sheet-like body formed from a pliable material, and includes an outward-facing surface that is substantially opaque to UVC light and an inward-facing surface that is to be arranged opposite a surface of the object to be decontaminated. A plurality of UVC sources are exposed at the inward-facing surface, and a plurality of spacers are arranged among the UVC sources to maintain a suitable separation between the UVC sources and the surface of the object to be decontaminated. This suitable separation promotes complete coverage of the surface with UVC light emitted by the UVC sources.

8 Claims, 2 Drawing Sheets

(56) References Cited

U.S. PATENT DOCUMENTS

| | | | | |
|---|---|---|---|---|
| 2008/0071330 A1* | 3/2008 | Quisenberry | ............. | A61F 7/02 607/88 |
| 2011/0278467 A1* | 11/2011 | Tanaka | .................... | C02F 1/325 250/372 |
| 2012/0191031 A1* | 7/2012 | Quisenberry | ............. | A61F 7/02 604/20 |
| 2012/0259266 A1* | 10/2012 | Quisenberry | ............. | A61F 7/02 604/20 |
| 2014/0257175 A1* | 9/2014 | Quisenberry | ......... | A61M 35/00 604/24 |
| 2015/0360606 A1* | 12/2015 | Thompson | ............. | B60Q 3/252 362/490 |

FOREIGN PATENT DOCUMENTS

| | | | |
|---|---|---|---|
| KR | 20140065028 A * | 5/2014 | |
| RU | 2106848 | 3/1998 | |
| RU | 2106848 C1 * | 3/1998 | |

* cited by examiner

DECONTAMINATION COVER FOR DECONTAMINATING AN OBJECT

BACKGROUND OF THE INVENTION

1. Field of the Invention

This application relates generally to an apparatus for rendering an object pathogen reduced and, more particularly, to a flexible cover or blanket including a plurality of ultraviolet light sources that, when illuminated, irradiate ultraviolet light onto an object on which the cover is placed.

2. Description of Related Art

Hospitals and other healthcare environments commonly include objects such as infusion pumps, keyboards, bed rails, remote controls, for example, that come into contact with sick patients, medical personnel treating sick patients, or other sources of pathogens. Pathogens transferred to such objects may subsequently spread to different patients and medical personnel unless the surfaces of those objects are properly cleaned and disinfected between uses involving different patients and/or medical personnel.

To clean the surfaces of objects in healthcare environments a towelette moistened with a chemical disinfectant is typically utilized to moisten the surface to be disinfected. The surface must remain moistened for at least three minutes for the disinfectant to adequately deactivate a suitable percentage of the population of pathogens present on the surface, thereby preventing the pathogens from infecting other patients and medical personnel. However, such a process requires a large supply of single-use towelettes, which become waste after each use, and requires the close attention of the person cleaning the surfaces to ensure that the surfaces remain wet with the disinfectant for at least the minimum length of time mandated by the specific towelettes being used. Additionally, many objects are not planar, making it difficult to wet all of the various contours, joints between surface, and other hard-to-reach places with the chemical disinfectant.

BRIEF SUMMARY OF THE INVENTION

According to one aspect, the subject application involves a decontamination cover to be applied over an object to be decontaminated. The decontamination cover includes a sheet-like body formed from a pliable material, and includes an outward-facing surface that is substantially opaque to UVC light and an inward-facing surface that is to be arranged opposite a surface of the object to be decontaminated. A plurality of UVC sources are exposed at the inward-facing surface, and a plurality of spacers are arranged among the UVC sources to maintain a suitable separation between the UVC sources and the surface of the object to be decontaminated. This suitable separation promotes complete coverage of the surface with UVC light emitted by the UVC sources.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
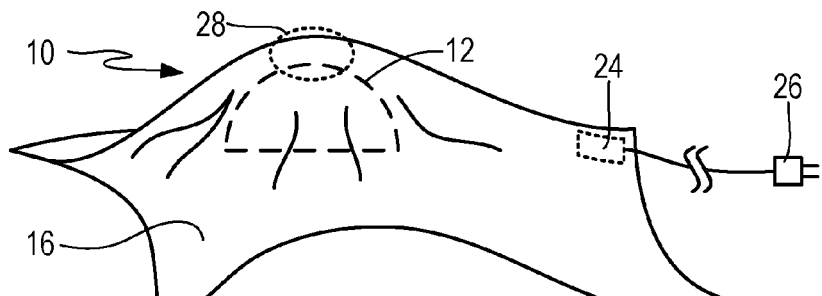
FIG. 1 shows an illustrative embodiment of a decontamination cover draped over an object with an exposed surface being decontaminated.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

An illustrative embodiment of a decontamination cover, interchangeably referred to herein as a blanket 10 for brevity, draped over an object 12 with an exposed surface 14 (FIG. 3) being rendered pathogen reduced is shown in FIG. 1. To be rendered "pathogen reduced", at least a portion, optionally less than all, of a biologically-active organisms present on the exposed surface 14 of the object 12 is deactivated. For instance, rendering the object 12 pathogen reduced does not necessarily require the object 12 to be made 100% sterile, free of any and all biologically-active organisms that can viably infect a human being. Instead, being rendered pathogen reduced requires a lower level of biologically-active contagions viable to cause an infection to remain on the surface 14 of the object 12 after performance of the decontamination process herein than existed on the surface 14 prior to performance of the decontamination process. Also, deactivation of the biologically-active contagions can include killing live contagions, or at least neutralizing their ability (e.g., rendering them no longer viable) to reproduce to an extent that results in an infection in a human exposed to the deactivated contagions.

According to other embodiments, the surface 14 can be required to possess a lower level of viable or otherwise biologically-active contagions than a threshold quantity permitted under U.S. Food and Drug Administration requirements on objects dedicated for use in a sterile field, such as in an operating room during a surgical procedure, for example. According to other embodiments, the decontamination process can be required to kill or otherwise deactivate at least 99% of all living or otherwise biologically-active contagions present on the surface 14 immediately prior to performance of the decontamination process to render the surface 14 pathogen reduced. According to yet other embodiments, achieving high-level disinfection of the surface 14 utilizing the blanket 10 can involve deactivation of a suitable portion of the biologically-active contagions to achieve at least a 1 $\log_{10}$ reduction of viable contagions on the object that remain infectious (i.e., no more than 1/10th of the biologically-active contagions on the surface 14 remain active or infectious at a time when the decontamination process is completed). According to yet other embodiments, achieving high-level disinfection of the surface 14 utilizing the blanket 10 can involve deactivation of a suitable portion of the biologically-active contagions to achieve at least a 3 $\log_{10}$ reduction (i.e., 1/1,000th) of viable contagions on the object. According to yet other embodiments, achieving high-level disinfection of the surface 14 utilizing the blanket 10 can involve deactivation of a suitable portion of the biologically-active contagions to achieve at least a 5 $\log_{10}$ reduction (i.e., 1/100,000th) of viable contagions on the object.

Similarly, sterilization of the surface 14 utilizing the blanket 10 can involve deactivation of a suitable portion of the biologically-active contagions to achieve at least a 6 $\log_{10}$ reduction (i.e., 1/1,000,000th) of viable contagions on the surface 14. Yet other embodiments requiring sterilization of the object can result in a complete and total deactivation of viable organisms on the surface 14 through performance of the decontamination process.

Regardless of the level of decontamination, use of the blanket 10 subjects the surface 14 of the object 12 to a decontamination process that at least disinfects, and optionally sterilizes the object 12 by exposing the surface 14 to a disinfectant which, in the present embodiment is ultraviolet-C ("UVC") light, to deactivate (e.g., kill or otherwise render no longer viable to cause an infection) a portion of a biologically-active contaminant present on the surface 14 exposed to the disinfectant. Once the decontamination process is complete, the object is considered suitable for use in a sterile field such as a patient's hospital room, an operating room during a surgical procedure, or other healthcare-related setting.

Referring once again to FIG. 1, the blanket 10 includes an outward-facing surface 16 that is opaque to UVC light. The outward-facing surface 16 serves as a shield, to interfere with the transmission of UVC light emitted by the UVC sources 18 (FIG. 2) in a direction generally away from the object 12 during a decontamination process. Thus, when draped over the object 12, or wrapped around the object 12, the outward-facing surface 16 remains visible to observers. Since the outward-facing surface 16 and/or underlying material is opaque to UVC light, observers will not be exposed to the UVC light emitted by the UVC sources 18. According to alternate embodiments, the blanket 10 can further include a separate light shield made of material opaque to UVC light. For such embodiments, the separate shield can be draped on top of and/or wrapped around an embodiment of the blanket 10 that lacks the opaque outward-facing surface 16 after the blanket 10 has been draped over, wrapped around, or otherwise applied to the object 12 to be decontaminated.

Figure 2:
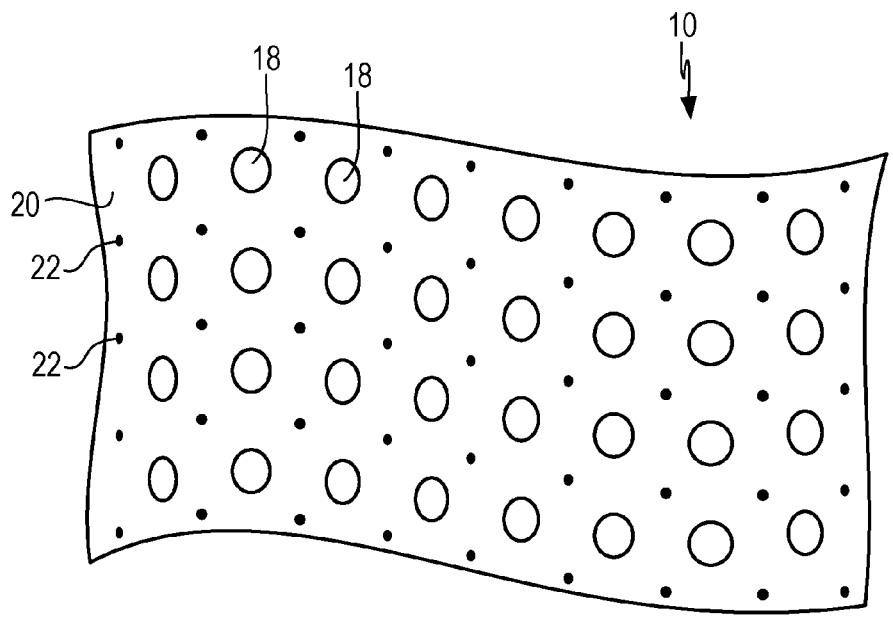
FIG. 2 shows an illustrative embodiment of a bottom surface of a decontamination cover comprising an array of ultraviolet-emitting LED sources and an array of spacers.

An inward-facing surface 20 of the blanket 10 is shown in FIG. 2. The inward-facing surface 20 is the surface of the blanket 10 that faces the object 12 being decontaminated by the blanket 10. As such, the inward-facing surface 20 includes a plurality of UVC sources 18, optionally arranged in a regular array, and a plurality of spacers 22, also optionally arranged in a regular array between the UVC sources 18. The inward-facing surface 20 can optionally be reflective, (e.g., polished mylar) to focus any reflected UVC light emitted by the UVC sources generally toward the surface 14.

Each UVC source 18 emits UVC light (e.g., with a wavelength of approximately 200 nm to approximately 280 nm) while operational, and is suitably durable to withstand flexing of the blanket 10 without being damaged to an extent that would render them inoperable to emit UVC light. Each UVC source 18 can include a UVC light emitting diode ("UVC LED"), which is a solid-state device formed on semiconducting substrates or other suitable substrates such as aluminum nitride, for example, that emits UVC light when energized. The UVC sources 18 can optionally be recessed inward (e.g., in a direction generally toward the outward-facing surface 20) from the inward-facing surface 20. Regardless of whether the UVC sources 18 are recessed, they are exposed at the inward-facing surface to emit UVC light toward the exposed surface 14 of the object 12.

Electric energy for energizing each of the UVC sources 18 can be supplied by a power supply 24 provided to a controller, shown in FIG. 1 as being supported by the blanket 10. The power supply 24 can be a portable, self-contained source of electric energy to be supplied to the UVC sources 18 such as a rechargeable and/or replaceable battery. According to alternate embodiments, the power supply 24 can include circuit components that are operable to condition (e.g., rectify, amplify, lower, etc . . . ) electric energy from an external source such as an AC mains wall outlet supplied by a local electric utility. For such embodiments, a plug 26 can optionally extend from the power supply 24 to an AC mains wall outlet to recharge a battery, conduct electric energy to the circuit components, etc . . . . The plug 26 can optionally be made detachable and re-attachable to a socket provided to the blanket 10 in electric communication with the power supply 24, allowing the plug 26 to be connected as needed to recharge a battery or conduct electric energy to the power supply 24 for energizing the UVC sources 18. The circuit components can optionally also be configured to create a timer that terminates operation of the UVC sources 18 and/or issues an alert after a predetermined period of time elapses to indicate the completion of a decontamination process. Further, the circuit components can optionally include at least one sensor such as an accelerometer, for example, that can detect movement of the decontamination cover 10 while the UVC sources 18 are active. In response, the UVC sources 18 can be terminated by the controller to avoid exposing people to the UVC light. A non-transitory computer-readable memory that stores information indicative of the performance of decontamination processes by the decontamination cover 10, for example, can also be formed as part of the circuit components. For example, the memory can store data indicating at least one of: whether a decontamination process was prematurely interrupted before the process was complete, a number of decontamination processes performed, a runtime of the UVC sources 18, and other such data relating to the performance of decontamination processes.

Although shown supported on the blanket 10 itself, the power supply 24 can also be located remotely from, but operatively connected to conduct electric energy to the UVC sources 18 provided to the blanket 10. For example, an external battery pack can be connected to the blanket 10 and replaced by another battery pack, as needed, to allow for minimal interruptions in the blanket's usage when one battery becomes depleted of energy. As another example, a so-called "wall wart" type AC/DC adapter including a housing that is separate from the blanket and contains the electric circuit components to rectify AC electric energy into DC electric energy can be located remotely from the blanket 10 and used to energize the UVC sources 18.

Figure 3:
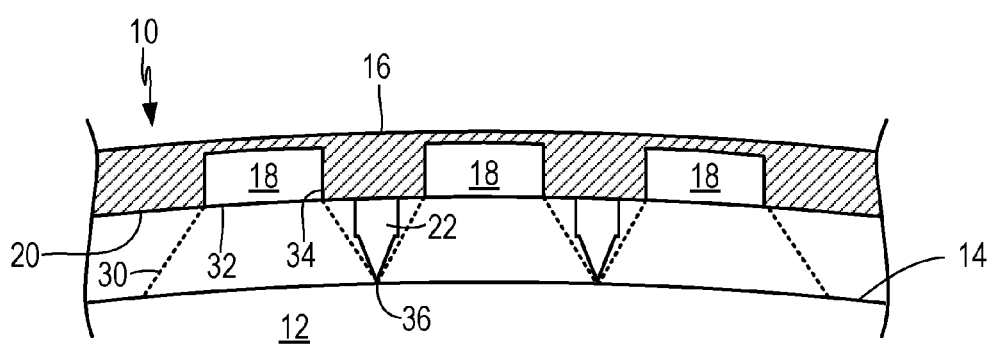
FIG. 3 shows a partially cutaway view of a region of the decontamination cover draped over the object encircled in FIG. 1.

As shown in FIG. 2, the UVC sources 18 are arranged in a regular array, distributed entirely over the lateral and longitudinal extents of the blanket 10. The spacers 28 are arranged amongst the UVC sources 18. FIG. 3 shows a magnified view of the portion of the interface between the blanket 10 and the surface 14 of the object 12 being decontaminated identified by the outline 28 appearing in FIG. 1. As shown in FIG. 3, the lateral spacing UVC sources 18 apart from each other in conjunction with the distance that the inward-facing surface 20, and accordingly, the UVC sources 18 are supported above the surface 14 to promote full coverage of the surface 18 with UVC light 30. For the illustrated embodiment, an exterior surface or lens 32 of the UVC sources 18 is substantially flush with the inward-facing surface 20 to minimize the interference with emission of UVC light laterally outward, beyond the perimeter 34 of the UVC sources 18. The spacers 22 position the lens 32 of each UVC source 18 illuminating the surface 14 a predetermined distance away from the surface 14 to allow the UVC light 30 emitted by the UVC sources 18 to radiate outwardly, beyond the perimeter 34 of the UVC sources 18. However, this separation is limited, to ensure the intensity of the UVC light 30 reaching the surface 14 is suitable to achieve the desired level of decontamination within a predetermined period of time. Thus, as shown in FIG. 3, the cross section of the UVC light 30 emission is represented by a somewhat trapezoidal shape, with a region of coverage at the surface 14 that extends beyond the dimensions of the UVC sources 18.

According to alternate embodiments, the distal end 36 of each spacer 22 can be formed into a point, with a minimal footprint to minimize the area of the surface 14 shaded from the UVC light 30 emitted by the UVC sources 18. According to alternate embodiments, the spacers 22, or portions thereof (e.g., the pointed distal end 36), can be formed from a material that is substantially transparent to UVC light 30, allowing unobstructed illumination of the surface 14 by the UVC light 30.

Figure 4:
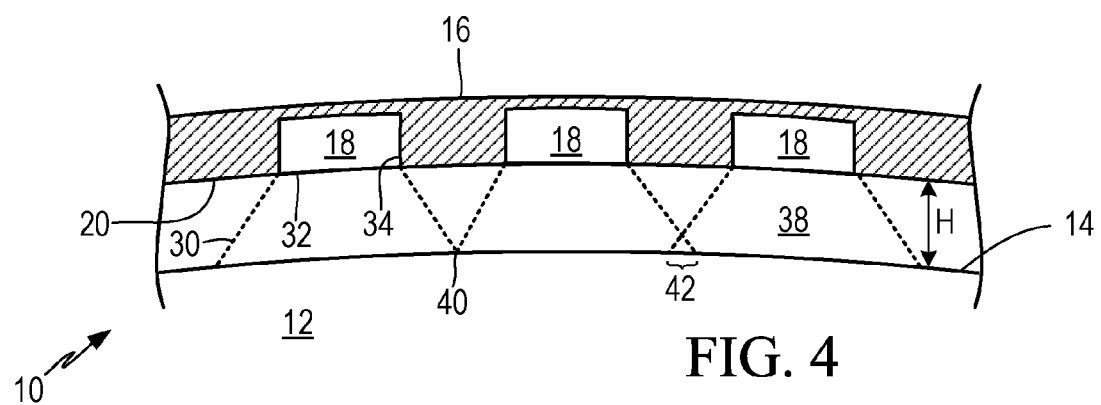
FIG. 4 shows a partially cutaway view of a region of an alternate embodiment of a decontamination cover draped over the object encircled in FIG. 1.

An alternate embodiment of a blanket 10 section is shown in FIG. 4. According to such an embodiment, instead of the supports 22, a continuous, uninterrupted layer or sheet of material 38 can be coupled, adhered, or otherwise applied to the inward-facing surface 20. This layer of material 38 can optionally have a height H, when measure with the blanket 10 spread over a flat surface, suitable to allow UVC light emitted by neighboring UVC sources 18 to at least converge toward a common point 40, or optionally overlap to form an overlapping region 42 on the surface 14. For such embodiments, the height H of the layer of material 38 is selected as a function of the angle of UVC light emission of the neighboring UVC sources 18, as well as the distance separating the neighboring UVC sources 18. The embodiments utilizing the spacers 22 can be similarly configured (e.g., height of the spacers 22, distance separating neighboring UVC sources 18, angle of UVC light emission of each neighboring UVC source 18, etc.) to achieve the convergence of the UVC light towards the common point 40 or create overlapping regions 42 to ensure complete coverage of the surface 14 with UVC light emitted by neighboring LED sources 18.

Figure 5:
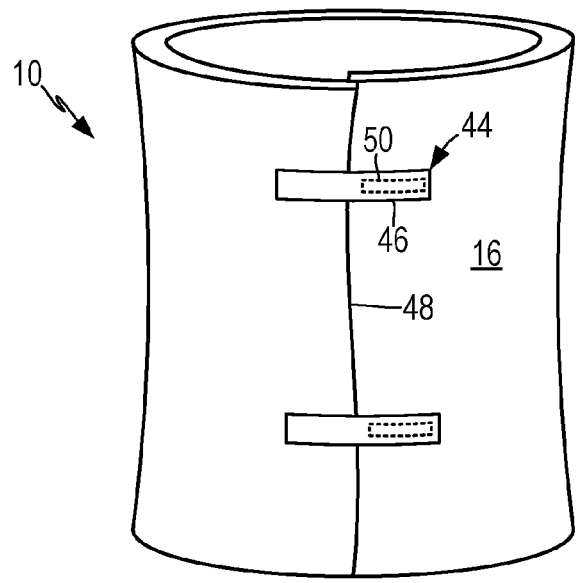
FIG. 5 shows a decontamination cover wrapped about an object and coupled to itself to at least encircle the object.

In use, the blanket 10 can be draped over and/or wrapped around the object 12 to be decontaminated, with the inward-facing surface 20 opposing the surface 14 of the object. As shown in FIG. 5, a hook and loop fastener system 44 or other releasable fastener, and/or the optional separate light shield can optionally be used to maintain the position of the blanket 10 on the object, and to interfere with the emission of UVC light away from the object 12. According to the embodiment shown in FIG. 5, the hook and loop fastener system 44 includes at least one, and optionally a plurality of flexible tabs 46 coupled to a first end 48 of the decontamination cover 10, but extend beyond that first end 48. An underside of each tab 46 includes a first material (e.g., hook material) 50, shown in hidden lines in FIG. 5, and the outward-facing surface 16 can be provided with a region including a second material that cooperates with the first material to establish a connection between the two. For example, the outward-facing surface 16 can optionally be formed of a fabric that constitutes the "loop" material of the hook and loop fastener system 44.

When the decontamination cover 10 is wrapped around the object 12, the hook and loop fastener system 44 or other coupling couples a portion of the decontamination cover 10 to itself, thereby holding the decontamination cover 10 in place. The spacers 22 establish the desired spacing between the UVC sources 18 and the surface 14 to be decontaminated, and the UVC sources 18 emit the UVC light to deactivate an acceptable portion of the biologically-active contagions on the surface 14 to render the surface 14 pathogen reduced for its intended use.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A decontamination cover to be applied over an object to be decontaminated, the decontamination cover comprising:
    a sheet-like body comprising a pliable material, an outward-facing surface that is substantially opaque to UVC light and an inward-facing surface that is to be arranged opposite at least a portion of a surface of the object to be decontaminated;
    a plurality of UVC sources arranged in an array located between the outward-facing surface and the inward-facing surface, wherein the UVC sources are exposed and emit the UVC light through lenses provided to the inward-facing surface; and
    a plurality of spacers extending from the inward-facing surface, wherein the plurality of spacers are arranged in a second array and distributed over the inward-facing surface between the lenses of the UVC sources, wherein the plurality of spacers are arranged to extend between the inward-facing surface of the sheet-like body and the object while the decontamination cover is applied to the object to establish a suitable separation between the UVC sources and the surface of the object that promotes complete coverage of the portion of the surface with UVC light emitted by the UVC sources.

2. The decontamination cover of claim 1, wherein the inward-facing surface comprises a reflective material that directs the UVC light generally toward the surface.

3. The decontamination cover of claim 1, wherein at least a portion of each of the plurality of spacers is formed from a material that is substantially transparent to the UVC light emitted by the UVC sources.

4. The decontamination cover of claim 3, wherein the UVC sources comprise UVC light emitting diodes.

5. The decontamination cover of claim 1, wherein the spacers comprise a height suitable to cause the UVC light emitted by neighboring UVC sources to converge at least to a common point on the surface of the object to be decontaminated.

6. The decontamination cover of claim 1, wherein the spacers comprise a height suitable to cause the UVC light emitted by neighboring UVC sources to overlap and form an overlapping region on the surface of the object to be decontaminated that is exposed to light emitted by each of the neighboring UVC sources.

7. The decontamination cover of claim 1 further comprising a releasable fastener that couples a first portion of the sheet-like body to a second portion of the sheet-like body.

8. The decontamination cover of claim 7, wherein the releasable fastener comprises a hook-and-loop fastening system and the second portion of the sheet-like body comprises a region of the outward-facing surface comprising a fastener material forming a portion of the hook-and-loop fastener system.

* * * * *